(12) United States Patent
Dong et al.

(10) Patent No.: US 10,534,359 B2
(45) Date of Patent: Jan. 14, 2020

(54) AIRCRAFT MANAGEMENT SYSTEMS AND METHODS FOR ECS PREDICTIVE MAINTENANCE

(71) Applicant: HONEYWELL INTERNATIONAL INC., Morris Plains, NJ (US)

(72) Inventors: Bin Dong, Beijing (CN); Qingqiu Ginger Shao, Oro Valley, AZ (US); Eric Shi, Shanghai (CN); Kyusung Kim, Plymouth, MN (US); Jinkun Liu, Shanghai (CN); Wenyan Guo, Shanghai (CN)

(73) Assignee: HONEYWELL INTERNATIONAL INC., Morris Plains, NJ (US)

(*) Notice: Subject to any disclaimer, the term of this patent is extended or adjusted under 35 U.S.C. 154(b) by 371 days.

(21) Appl. No.: 15/402,871

(22) Filed: Jan. 10, 2017

(65) Prior Publication Data

US 2018/0197351 A1 Jul. 12, 2018

(51) Int. Cl.
*G05B 23/02* (2006.01)
*G07C 5/00* (2006.01)
(Continued)

(52) U.S. Cl.
CPC ......... *G05B 23/0254* (2013.01); *B64D 13/02* (2013.01); *B64D 13/08* (2013.01);
(Continued)

(58) Field of Classification Search
CPC ............ G05B 23/0254; G05B 23/0283; G05B 2219/2638; G05B 2219/2614;
(Continued)

(56) References Cited

U.S. PATENT DOCUMENTS 5,369,959 A 12/1994 Pfefferle
6,386,272 B1 5/2002 Starner et al.
(Continued)

FOREIGN PATENT DOCUMENTS

EP 2327628 A2 6/2011
EP 2682835 A2 1/2014
(Continued)

OTHER PUBLICATIONS

USPTO Office Action for U.S. Appl. No. 15/402,910 dated Feb. 8, 2018.
(Continued)

*Primary Examiner* — Jelani A Smith
*Assistant Examiner* — Kelly D Williams
(74) *Attorney, Agent, or Firm* — Lorenz & Kopf, LLP

(57) ABSTRACT

A vehicle management system includes an onboard vehicle system and a ground system. The onboard vehicle system includes a compressor exit temperature sensor configured to determine an ECS compressor exit temperature; a data acquisition unit coupled to receive the compressor exit temperature, an altitude of the first vehicle, and an ambient temperature and configured to generate a data report; and a communications system coupled to receive and transmit the data report. The ground system includes a ground data server coupled to receive the data report and determine a fouling condition of an environmental conditioning element of the ECS based on at least the compressor exit temperature, the altitude, and the ambient temperature; and a mobile application module coupled to receive the fouling condition from the ground data server and configured to provide an interface for displaying the fouling condition to a user on a mobile device.

20 Claims, 8 Drawing Sheets

(51) Int. Cl.
*B64D 45/00* (2006.01)
*B64D 13/08* (2006.01)
*B64D 13/02* (2006.01)
*B64D 13/06* (2006.01)
*G01N 17/00* (2006.01)
*B64F 5/60* (2017.01)
*B64F 5/40* (2017.01)

(52) U.S. Cl.
CPC ............... *B64D 45/00* (2013.01); *B64F 5/40* (2017.01); *B64F 5/60* (2017.01); *G05B 23/0283* (2013.01); *G07C 5/008* (2013.01); *B64D 2013/0603* (2013.01); *B64D 2045/0085* (2013.01); *G01N 17/008* (2013.01); *G05B 2219/2614* (2013.01); *G05B 2219/2638* (2013.01); *G05B 2219/45071* (2013.01)

(58) Field of Classification Search
CPC .......... G05B 2219/45071; B64D 45/00; B64D 13/02; B64D 13/08; B64D 2045/0085; B64D 2013/0603; G01N 17/008; G07C 5/008; B64F 5/40; B64F 5/60
See application file for complete search history.

(56) References Cited

U.S. PATENT DOCUMENTS

| | | | |
|---|---|---|---|
| 6,708,507 | B1 | 3/2004 | Sem |
| 7,827,006 | B2 | 11/2010 | Miller |
| 9,316,178 | B2 | 4/2016 | Hagen |
| 9,724,979 | B1 | 8/2017 | Thumati et al. |
| 9,776,731 | B1 | 10/2017 | Lieberman et al. |
| 9,784,638 | B1 | 10/2017 | Followell et al. |
| 2010/0042445 | A1* | 2/2010 | Nicosia .......... G06Q 10/063114 705/7.15 |
| 2014/0008035 | A1 | 1/2014 | Patankar et al. |
| 2015/0121842 | A1 | 5/2015 | Moes |
| 2016/0144983 | A1 | 5/2016 | Thuong |
| 2016/0146487 | A1 | 5/2016 | Zywiak et al. |
| 2016/0273379 | A1 | 9/2016 | Soares, Jr. |
| 2016/0305865 | A1 | 10/2016 | Silva et al. |
| 2016/0320291 | A1 | 11/2016 | Najjar et al. |
| 2017/0370280 | A1 | 12/2017 | Lock |
| 2018/0051945 | A1* | 2/2018 | Hanov ................... F28F 27/00 |
| 2018/0057170 | A1 | 3/2018 | Sautron |
| 2018/0086471 | A1 | 3/2018 | Wollenweber |
| 2018/0148182 | A1 | 5/2018 | Fagundes |
| 2018/0155061 | A1 | 6/2018 | Bewlay |
| 2018/0194487 | A1 | 7/2018 | Flynn |

FOREIGN PATENT DOCUMENTS

| | | |
|---|---|---|
| EP | 2722693 A1 | 4/2014 |
| GB | 2502276 A | 11/2013 |
| RU | 2241641 C1 | 12/2004 |
| WO | 2015124889 A1 | 8/2015 |

OTHER PUBLICATIONS

Extended EP Search Report for Application No. 18150638.7 dated Apr. 30, 2018.
Shah, Shoaib, et al. "On-Line Fouling Detection of Aircraft Environmental Control System Cross Flow Heat Exchanger," Mechatronics and Automation, 2009, ICMA 2009, International Conference on Aug. 1, 2009.
Extended EP Search Report for Application No. 18150620.5 dated May 2, 2018.
USPTO Final Office Action for U.S. Appl. No. 15/402,910 dated Jun. 29, 2018.
Nayeff Najjar, et al.; Optimal Sensor Selection and Fusion for Heat Exchanger Fouling Diagnosis in Aerospace Systems, IEEE Sensors Journal, vol. 16. No. 12, Jun. 15, 2016.
EP Examination Report for Application No. 18150638.7 dated Sep. 18, 2018.
USPTO Notice of Allowance for U.S. Appl. No. 15/402,910 dated Nov. 6, 2018.

* cited by examiner

AIRCRAFT MANAGEMENT SYSTEMS AND METHODS FOR ECS PREDICTIVE MAINTENANCE

TECHNICAL FIELD

The present invention generally relates to aircraft maintenance systems and methods, and more particularly relates to aircraft maintenance systems and methods for the heat exchangers of air conditioning packs in environmental control systems (ECS).

BACKGROUND

Aircraft operate in various types of geographical areas, including areas with elevated levels of pollution. Pollutants may include dust, particulates, and other types of contaminants. As such, aircraft typically include an environmental control system (ECS) that functions to condition and filter the air and supply clean, pollution-free air to interior spaces, such as the main cabin area. Over time, pollutants accumulate in the elements of the ECS, and eventually, these elements must be serviced or replaced in a maintenance operation. One type of element that occasionally requires maintenance is the heat exchanger. However, accurately predicting the appropriate time for the maintenance operation and replacement may be challenging. Premature replacement may result in unnecessary downtime and cost, while delayed replacement may result in operational inefficiencies and passenger discomfort.

Accordingly, it is desirable to provide improved maintenance systems and methods that enable more timely and accurate replacement of ECS elements, particularly heat exchangers, to minimize disruption and improve efficiency. Furthermore, other desirable features and characteristics of the present invention will become apparent from the subsequent detailed description of the invention and the appended claims, taken in conjunction with the accompanying drawings and this background of the invention.

BRIEF SUMMARY

In accordance with an exemplary embodiment, a vehicle management system includes an onboard vehicle system arranged onboard a first vehicle and a ground system. The onboard vehicle system includes a compressor exit temperature sensor configured to determine a compressor exit temperature at a compressor of an environmental control system (ECS) of the first vehicle; a data acquisition unit coupled to receive the compressor exit temperature from the compressor exit temperature sensor, an altitude of the first vehicle, and an ambient temperature, and configured to generate a data report containing at least the compressor exit temperature, the altitude, and the ambient temperature; and a communications system coupled to receive and transmit the data report from the data acquisition unit. The ground system includes a ground data server coupled to receive the data report from the communications system, the ground data server configured to determine a fouling condition of an environmental conditioning element of the ECS based on at least the compressor exit temperature, the altitude, and the ambient temperature; and a mobile application module coupled to receive the fouling condition from the ground data server and configured to provide an interface for displaying the fouling condition to a user on a mobile device.

In accordance with another exemplary embodiment, a method includes collecting, with an onboard vehicle system for a first vehicle, a compressor exit temperature of a compressor of a heat exchanger of an environmental control system (ECS) of the first vehicle, an altitude of the first vehicle, and an ambient temperature; generating a data report with the compressor exit temperature, the altitude, and the ambient temperature; sending the data report with a communications system; receiving, at a ground data server, the data report from the communications system; determining a fouling condition of the heat exchanger of the ECS based on at least the compressor exit temperature, the altitude, and the ambient temperature; and generating a user report on a mobile application interface for displaying the fouling condition to a user on a mobile device.

BRIEF DESCRIPTION OF THE DRAWINGS

The present invention will hereinafter be described in conjunction with the following drawing figures, wherein like numerals denote like elements.

DETAILED DESCRIPTION

Figure 1:
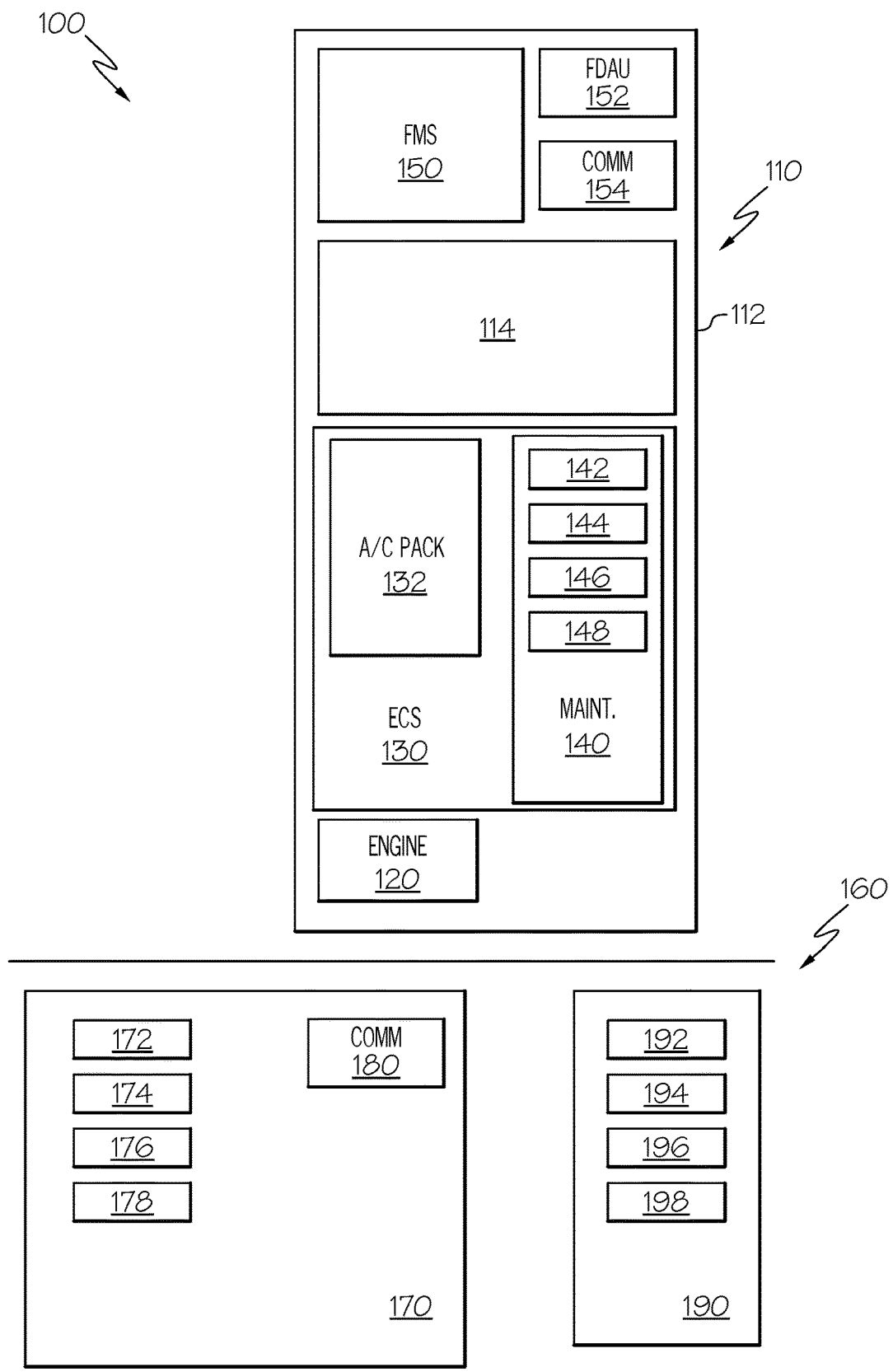
FIG. 1 is a schematic block diagram of an aircraft management system in accordance with an exemplary embodiment.

The following detailed description is merely exemplary in nature and is not intended to limit the invention or the application and uses of the invention. As used herein, the word "exemplary" means "serving as an example, instance, or illustration." Thus, any embodiment described herein as "exemplary" is not necessarily to be construed as preferred or advantageous over other embodiments. All of the embodiments described herein are exemplary embodiments provided to enable persons skilled in the art to make or use the invention and not to limit the scope of the invention which is defined by the claims. Furthermore, there is no intention to be bound by any expressed or implied theory presented in the preceding technical field, background, brief summary, or the following detailed description.

Exemplary embodiments discussed below provide systems and methods that monitor and manage heat exchangers in the air conditioning packs of the environmental control systems (ECS) to generate fouling predictions, trends, and/ or diagnostics. In particular, condition and health indicators are generated based on one or more parameters to represent the current and future conditions of the heat exchangers. For example, one issue is "fouling" in which pollutants in the air flow accumulate over time in the heat exchangers, and in consideration of this issue, exemplary embodiments may generate a fouling condition representing a degree of fouling of the respective heat exchanger. In some embodiments, this fouling condition may be expressed as a "fouling factor" that provides a numerical value representing the degree of the fouling condition of the respective heat exchanger. Any representation of a fouling factor may be provided, although in one example, the fouling factor is scaled to be between 0.0 and 1.0, with 0.0 being a completely new and unfouled heat exchanger and 1.0 being a completely fouled heat exchanger. The fouling condition and/or fouling factor may also be qualitatively represented by predictive alerts that also indicate the severity of fouling. As examples, a value of less than 0.4 is a "green" condition or informational alert that indicates the level of fouling of the respective heat exchanger does not warrant action. A value of 0.4-0.8 is a "yellow" condition or advisory alert that indicates the present level of fouling does not warrant action, but that it may in the short term future. A value of above 0.8 is a "red" condition or warning alert that indicates the present level of fouling should be addressed immediately.

Accordingly, in one embodiment, the green, yellow, and red conditions are determined based on the fouling factor range and function as a warning or prediction regarding the fouling status or other representation of the fouling condition of the heat exchanger. In effect, yellow and red conditions represent "advanced warnings" and connote the prediction of ECS functional conditions of an incipient fault detection. In addition to these conditions, the system and methods may also provide prognostics, such as the remaining useful life of a heat exchanger. As described in greater detail below, the fouling conditions may be considered with respect to an individual aircraft and/or multiple aircraft as part of an aircraft management system.

FIG. 1 is a schematic block diagram of certain features of an aircraft management system 100 in accordance with an exemplary embodiment. Generally, in one exemplary embodiment, the aircraft management system 100 may be considered to include one or more aircraft 110 and/or one or more aircraft systems located on the aircraft 110. Although one aircraft 110 is depicted in FIG. 1 and discussed with respect to the overall management system 100, the management system 100 may be considered to include more than one aircraft 110 and/or aircraft systems or just the single aircraft 110 and associated aircraft system. Unless otherwise noted, additional aircraft may be considered to include similar components to the ones discussed below with respect to aircraft 110. The aircraft management system 100 may further be considered to include, or otherwise interact with, a ground system 160 associated with the aircraft manufacturer, owner, airline, monitoring service, government, and/or industry group.

The features of the aircraft 110 depicted in FIG. 1 may be relevant to the exemplary embodiments described below. Although not shown and/or discussed in detail, the aircraft 110 may have any number of additional components typically used in the aerospace industry. In the illustrated embodiment, the aircraft 110 includes a fuselage 112, an engine 120, an environmental control system (ECS) 130, a flight management system (FMS) 150, a flight data acquisition unit 152, and a communications system 154. Even though the description below primarily references "aircraft" for efficiency, the systems and methods are not limited to aircraft and can also be implemented in other types of vehicles, including cars, trucks, ships, submarines, spacecraft, or unmanned vehicles. Each component of the aircraft management system 100 is introduced below prior to a more detailed description of particular aspects of operation.

Generally, the fuselage 112 is the main body of the aircraft 110 and may include or contain a cabin 114. As used herein, the term "cabin" refers to any interior space within the aircraft 110 that utilizes environmental control and houses passengers, crew, and/or electronic equipment. The aircraft 110 may further include an air intake apparatus (not shown) for directing air from the outer surface of the fuselage 112 to the engine 120 and/or the EC S 130, as described below. Other types of arrangements may be provided.

The engine 120 may include any type of system to provide energy to the aircraft 110 in the form of electricity and/or propulsion. In one exemplary embodiment, the engine 120 may be a turbofan or turboshaft engine, including a gas turbine engine. The engine 120 has an overall construction and operation that is generally understood by persons skilled in the art.

Generally, the ECS 130 includes various environmental conditioning elements configured to supply a relatively clean and conditioned flow of air (e.g., with the proper pressure, temperature, and humidity) to selected interior portions of the fuselage 112, particularly the cabin 114. As shown, the ECS 130 may be considered to include one or more air conditioning packs 132 (one of which is shown) and a maintenance system 140, although any number of additional components and/or elements may be provided.

As an introduction, in one exemplary embodiment, the air conditioning pack 132 receives a portion of the air from the engine 120, typically in the form of bleed air from a compressor section, and the air conditioning pack 132 includes one or more heat exchangers and other components to cool or otherwise condition the flow of air in terms of pressure, temperature, and/or humidity such that the air is suitable for the cabin 114. As noted above, the air flowing through the ECS 130 may include pollutants, such as dust, particulates, and/or contaminants. Although the ECS 130 includes components that function to remove these pollutants, the various components of the ECS 130 may be subject to fouling (e.g., pollutant accumulation over time). The exemplary embodiments discussed below are particularly applicable to monitor and predict the conditions associated with the fouling of the heat exchangers of the air conditioning pack 132.

Accordingly, the maintenance system 140 is used to monitor the condition or health characteristics of one or more aspects of the ECS 130 and provides support for an operator or other individual for use in making decisions regarding future maintenance, operation, or use of the aircraft 110. The discussion below refers to an operator or user as any individual interacting with and/or receiving information from the aircraft system 100, including flight crew, maintenance crew, and control centers. Depending on the context, the referenced user may vary. For example, and as discussed in greater detail below, monitoring of the ECS 130 may be relevant for the individual aircraft 110 or for the aircraft 110 as part of an overall fleet. As such, in some instances, the user may be the operator or maintenance crew responsible for the aircraft 110, while in other instances, the user may be an airline or fleet management operator that manages service and flight scheduling of a number of aircraft 110. In the discussion below, references to the user are applicable to either type.

In one exemplary embodiment, the maintenance system 140 particularly monitors the heat exchangers of the air conditioning pack 132, although the maintenance system 140 may also monitor other aspects of the ECS 130 and the overall aircraft 110. Generally, the maintenance system 140 receives data from various systems and subsystems of the aircraft system 100. As discussed below, the maintenance system 140 may receive data from the FMS 150, the flight data acquisition unit 152, and various sensors distributed in the ECS 130, as examples. Based on this data, the maintenance system 140 determines, aggregates, and monitors health and condition indicators, such as a fouling factor associated with the ECS 130.

In one exemplary embodiment, the maintenance system 140 may be embodied as a computer system with a processor 142, a memory 144, a storage device 146, and a user interface 148 coupled together in any suitable manner, such as a bus (not shown). Generally, processor 142 performs computation and control functions, and may be implemented with any type of processor or multiple processors, single integrated circuits such as a microprocessor, or any suitable number of integrated circuit devices and/or circuit boards working in cooperation to accomplish the functions described herein. During operation, the processor 142 executes one or more programs, typically stored within the memory 144 and, as such, controls the general operation of the maintenance system 140.

In one embodiment, the memory 144 stores a program or programs that execute one or more embodiments of a maintenance functions described in greater detail below. The memory 144 can be any type of suitable memory. The memory 144 may include one or more of various types of dynamic random access memory (DRAM) such as SDRAM, the various types of static RAM (SRAM), and the various types of non-volatile memory (PROM, EPROM, and flash). It should be understood that the memory 144 may be a single type of memory component, or it may be composed of many different types of memory components. In addition, the memory 144 and the processor 142 may be distributed across several different computers that collectively form the maintenance system 140. The memory 144 may also be considered to include any number of databases and/or data sources.

The storage device 146 may be any suitable type of storage apparatus, including direct access storage devices such as hard disk drives, flash systems, floppy disk drives and optical disk drives. In one exemplary embodiment, the storage device 146 is a program product from which memory 144 can receive a program that executes one or more embodiments to perform the functions described herein.

As introduced above, the maintenance system 140 may additionally include the user interface 148 that enables the operator to interact with the maintenance system 140. As examples, the user interface 148 may present user reports associated with the ECS 130. Accordingly, the user interface 148 may include any suitable hardware and software components. Such components may include keyboards, mouse devices, buttons, switches, levers, and knobs. The user interface 148 may include a display unit capable of displaying various types of computer generated symbols and information, such as various CRT or flat panel display systems, such as LCDs, OLED displays, projection displays, plasma displays, HDDs, HUDs, and the like. As described in greater detail below, the user interface 148 may particularly display monitoring information associated with the ECS 130, such as reports with condition and health indicators, fouling factors, and/or other relevant or desired information.

Notably, it should be understood that although maintenance system 140 appears in FIG. 1 to be arranged as an integrated system, the exemplary embodiments are not so limited and can also include an arrangement whereby one or more of the components are separate components or subcomponents of another system located either onboard or external to an aircraft. Additional details about the maintenance system 140 are provided below.

The FMS 150 generally performs a wide variety of in-flight tasks during operation of the aircraft 110. Although not specifically shown, the FMS 150 may include a navigation system and guidance system implemented with one or more computer processors, such as for example, a microprocessor or digital signal processor capable of performing the functions discussed herein. In general, the navigation system determines the current kinematic state of the aircraft. The guidance system provides the flight plan in the form of guidance commands to the auto-pilot system (not shown) and/or the operator for implementation and appropriate operation of the aircraft 110. The FMS 150 may further include a database with any elements necessary for the operation of the aircraft 110. Among other functions, the FMS 150 may provide the maintenance system 140 with various types of aircraft, operational, and/or environmental data. For example, the FMS 150 may provide the maintenance system 140 and/or the flight data acquisition unit 152 with operating conditions, such as the ambient temperature ($T_{amb}$) and the altitude (Alt) of the aircraft 110.

The flight data acquisition (and management) unit 152 functions to collect various types of aircraft information, including information from the engine 120, the ECS 130, and FMS 150. Other systems from which data may be collected include equipment and actuators, sensor and structural monitors, landing gear and brakes, and auxiliary power unit (APU). The flight data acquisition unit 152 may process, organize, aggregate, and/or otherwise prepare the data in a desired format for the communications system 154. As discussed in greater detail below, the various types of data associated with the heat exchangers of the air conditioning pack 132 are also made available to the flight data acquisition unit 152.

The aircraft 110 may further include a communications system 154. In one exemplary embodiment, the communications system 154 collects various types of aircraft information associated with the aircraft 110, for example, from the flight data acquisition unit 152. The communications system 154 transmits the aircraft information to the ground data server 170. The communications system 154 may operate according to any suitable communications protocol. In particular, the communications system 154 may be configured to establish a wireless communication link over a network. In one exemplary embodiment, the communications system 154 may be part of an aircraft communications addressing and reporting system (ACARS) that functions as a digital system for transmission of relatively short messages between aircraft and ground stations via airband radio or satellite.

The ground system 160 may include one or more ground data servers 170 in communication with one or more user devices 190. FIG. 1 depicts one ground data server 170 and one user device 190. In practice, however, any number of ground data servers 170 supporting any number of user devices 190 may be provided.

In one exemplary embodiment, the ground data server 170 receives the aircraft information from the aircraft 110, particularly from the communications system 154 of the aircraft 110. The ground data server 170 processes the data to calculate and/or extract the condition and health indicators associated with the ECS 130, particularly the heat exchangers of the ECS 130, as described in greater detail below. The ground data server 170 may prepare a user (or customer) report based on this information and provide the user report to one or more of the user devices 190, as also described in greater detail below. The user report may be associated with an individual aircraft or a group (or fleet) of aircraft.

In practice, according to one exemplary embodiment, the ground data server 170 may be embodied as a computer system with a processor 172, a memory 174, a storage device 176, and a user interface 178 coupled together in any suitable manner, such as a bus (not shown). Generally, these components operate in a similar manner to the analogous components discussed above with respect to the maintenance system 140. Additional details regarding the ground data server 170 will be provided below.

The ground data server 170 may further include a communications system 180. In one exemplary embodiment, the communications system 170 collects various types of aircraft information associated with the aircraft 110, as well as other aircraft. In one exemplary embodiment, the communications system 180 may be part of an ACARS arrangement. Additionally and as introduced above, the communications system 180 transmits data from the ground data server 170, including user reports, to the user devices 190. The communications system 180 may operate according to any suitable communications protocol to receive and transmit data, examples of which are discussed below.

The user device 190 may be any suitable type of device for receiving the user report from the ground data server 170. As examples, the user device 190 may be a personal computer, mobile telephone, tablet or other network-enabled user device on a network for accessing the ground data server 170. Operation of the device 190 may be implemented with software running on a hardware platform, for example, a general purpose or specialized computer, including a processor, and a computer readable medium (e.g., a memory and other storage devices such as CD, DVD, hard disk drive, etc.) having instructions stored thereon for execution. In FIG. 1, the user device 190 may be considered to operate with respect to a number of functional units 192, 194, 196, 198. The functional units include a control module 192, a maintenance module 194, a user interface 196, and a network interface 198. Generally, the control module 192 controls operation of the user device 190 and the user interface 196 enables the user to interact with the user device 190. The network interface 198 enables the device 190 to communicate with the ground data server 170 in any suitable manner, including via a public network, Internet, a Public Switched Telephone Network (PSTN), a mobile network, or any other network providing connectivity.

In one exemplary embodiment, the user device 190 is a mobile phone, tablet, smartphone, or other mobile user device 190 and the maintenance module 194 is a mobile application running on the mobile user device 190. As a result, the maintenance module 194 may present user reports via the user interface 196 on a display touch screen that enables viewing and user interaction with the report. Additional details about the user report are provided below.

In one exemplary embodiment, the user device 190 is a mobile phone, tablet, smartphone, or other mobile user device 190 and the maintenance module 194 is a mobile application running on the mobile user device 190. As a result, the mobile module 194 may present user reports via the user interface 196 on a display touch screen that enables viewing and user interaction with the report. Additional details about the user report are provided below.

Figure 2:
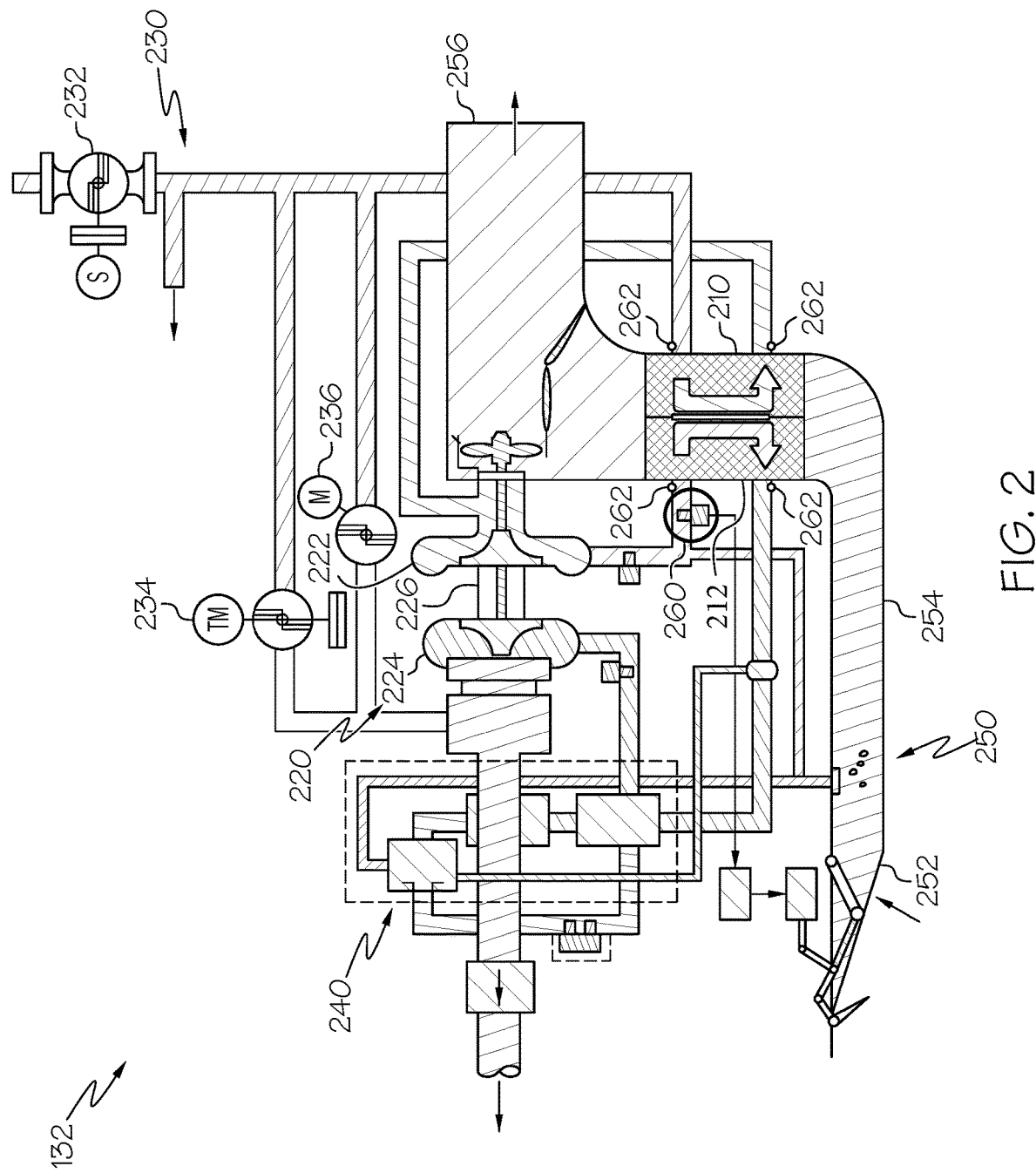
FIG. 2 is a schematic diagram of an air conditioning pack of an aircraft system of the management system of FIG. 1 in accordance with an exemplary embodiment.

FIG. 2 is an exemplary schematic view of an air conditioning pack, such as the air conditioning pack 132 of the aircraft 110 of FIG. 1. As shown, the air conditioning pack 132 includes a primary heat exchanger 210; a secondary heat exchanger 212; an air cycle machine 220 with a compressor 222 and turbine 224 coupled together via a shaft 226; a bleed control arrangement 230; a water management arrangement 240; and a ram air arrangement 250. It will be appreciated that additional components may be provided and/or certain components may be omitted and that the view of FIG. 2 is merely an example.

In one exemplary embodiment, air enters the air conditioning pack 132 via the bleed control arrangement 230 that may include a flow control valve 232 that controls the quantity and nature of the air flowing through the pack 132. As noted above, the air entering the air conditioning pack 132 may be bleed air from the engine 120 (FIG. 1), although the air conditioning pack 132 may receive air from other sources. Portions of the air may be directed to bypass the air cycle machine 220 as regulated by valves 234, 236, for example, to control temperatures and/or pressures of the air in the air conditioning pack 132, but generally, the air initially flows through the primary heat exchanger 210 where it is cooled by ram air of the ram air arrangement 250. In one exemplary embodiment, the ram air arrangement 250 receives air from outside of the aircraft via a ram air inlet 252 and the ram air flows through a ram air duct 254 for use in the heat exchangers 210, 212, after which the air is exhausted overboard via a ram air exhaust 256.

After passing through the primary heat exchanger 210, the cooled air then enters the compressor 222 where it is pressurized, thereby resulting in increased temperature. The air then passes through the secondary heat exchanger 212 where it is again cooled by ram air of the ram air arrangement 250. The air is then passed through the turbine 224, which expands the air to further reduce the temperature of the air and to extract mechanical power. Upstream of the turbine 224, the air may be directed through the water management arrangement 240 to remove water from the air, which may be exhausted into the ram air arrangement 250. Downstream of the turbine 224, the air is directed into the cabin and other portions of the aircraft for cooling.

The air conditioning pack 132 may include any number of sensors 260, 262 for collecting a variety of data, including data related to temperatures, pressures, flow rates and quantities, and valve positions throughout the air conditioning pack 132. In one exemplary embodiment, the sensors 260, 262 include one or more compressor exit temperature sensors 260 to measure the temperature of the air exiting the compressor 222 and one or more pressure sensors 262 to measure the pressure drop across one or both of the heat exchangers 210, 212. In some embodiments, the pressure sensors 262 may be omitted. The sensors 260, 262 may transmit the collected data to the maintenance system 140 via a wired or wireless connection, as described in greater detail below.

Figure 3:
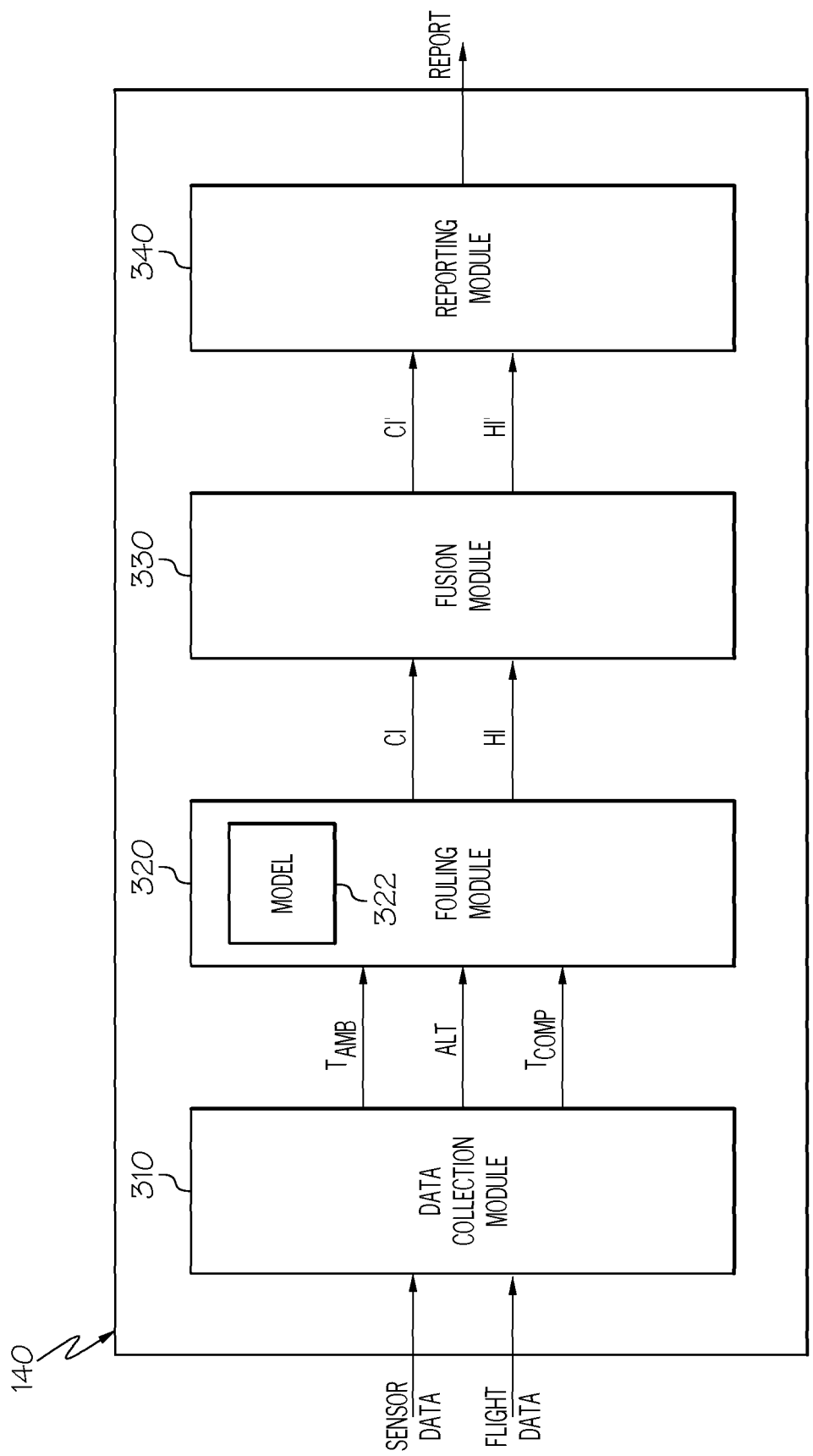
FIG. 3 is a functional block diagram of a maintenance system associated with an air conditioning pack of the aircraft system of FIG. 2 in accordance with an exemplary embodiment.

FIG. 3 is a more detailed functional block diagram of the maintenance system 140. FIG. 3 depicts the maintenance system 140 organized a number of functional units or modules 310, 320, 330, and 340 (e.g., software, hardware, or combinations thereof). Specifically, each of the modules 310, 320, 330, and 340 may be implemented by the components discussed above in FIG. 1 to carry out specific functions. FIG. 3 additionally depicts at least some of the data flows associated with the maintenance system 140, although further data flows are discussed in reference to FIGS. 4 and 5. FIG. 3 depicts one exemplary organization, and other embodiments may perform similar functions with alternative organization or implementation. FIG. 3 is described below with additional reference to FIGS. 1 and 2.

As noted above, the maintenance system 140 generally functions to evaluate the condition of the ECS 130, particularly one or more of the heat exchangers 210, 212 with respect to maintenance operations. As shown, the maintenance system 140 includes a data collection module 310. In one embodiment, the heat exchangers 210, 212 are considered individually, although other embodiments may be provided. Generally, the data collection module 310 is configured to collect the data that may be relevant to operation of the maintenance system 140. The data collection module 310 may receive any relevant information. In the depicted embodiment, the data collection module 310 receives sensor data and operating data.

In one exemplary embodiment, the data collection module 310 receives the sensor data from any of the various sensors, including sensors 260, 262 associated with the air conditioning pack 132. In particular, the sensor data may include the compressor exit temperature from sensor 260. In some embodiments, the sensor data may include differential pressure data associated with the heat exchangers 210, 212 from sensors 262. The operating data typically includes the current altitude and the ambient temperature received from the FMS 150 and/or the flight data acquisition unit 152.

In further embodiments, the data collection module 310 may receive data from various other sources, including data received from other aircraft systems or instruments and/or from command centers, airports, or other ground-based data sources. Other information may include identification information, pollution characteristics, geographical location, flight path characteristics, engine operating parameters, weather conditions, time dependencies, equipment characteristics, historical maintenance data, and other data, as some examples.

In the depicted embodiment, the data received by the data collection module 310 is relatively raw data from which the data collection module 310 may generate one or more values or parameters. As appropriate, the data collection module 310 may include any suitable type of conditioning and filtering functionality. As shown in FIG. 3, the data collection module 310 generates and/or otherwise provides parameters based on the received data. Such parameters may include at least one of a compressor exit temperature ($T_{comp}$), the altitude (Alt), and ambient temperature ($T_{amb}$).

Figure 4:
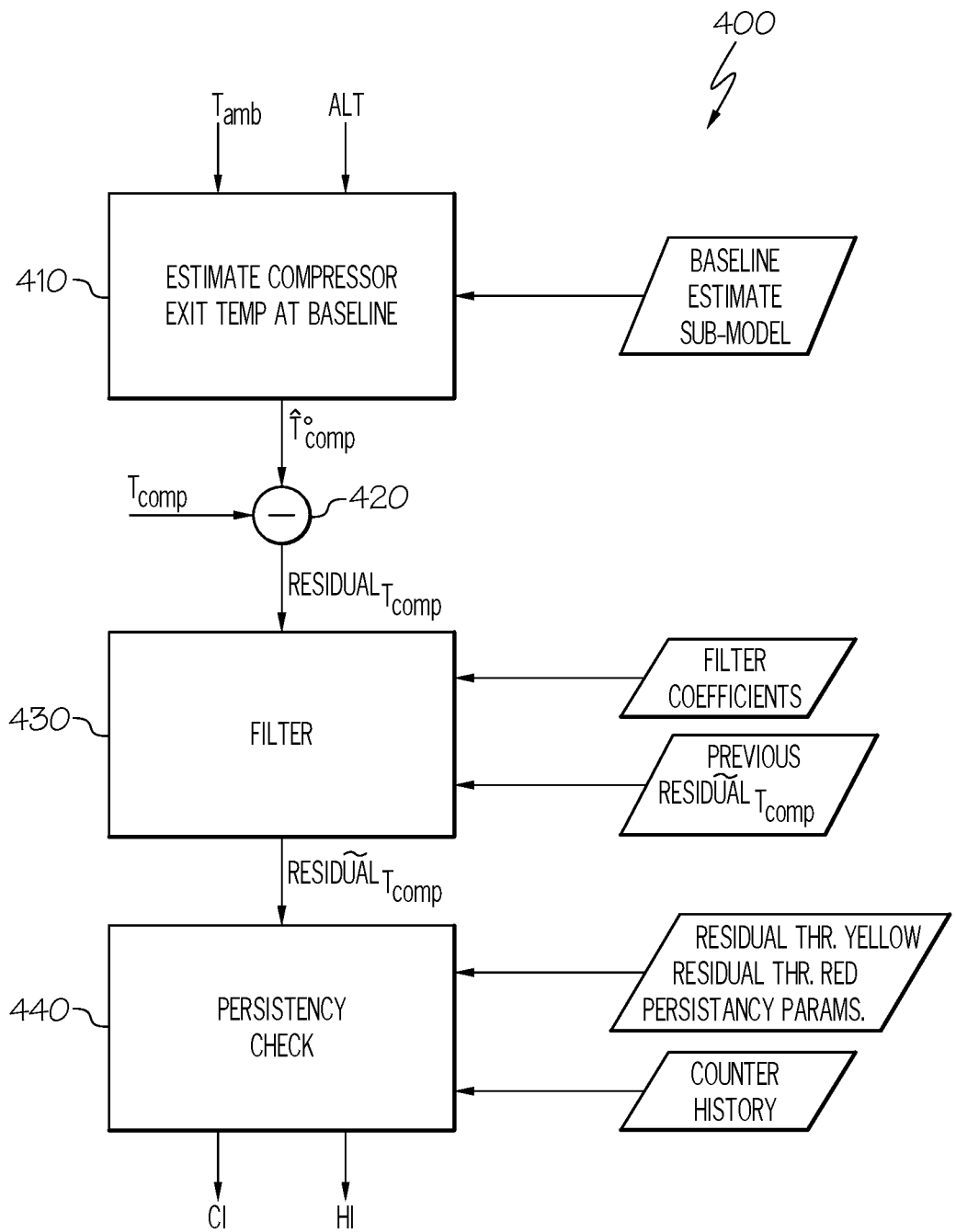
FIG. 4 is a functional block diagram of a fouling module of the maintenance system of FIG. 3 in accordance with an exemplary embodiment.
Figure 5:
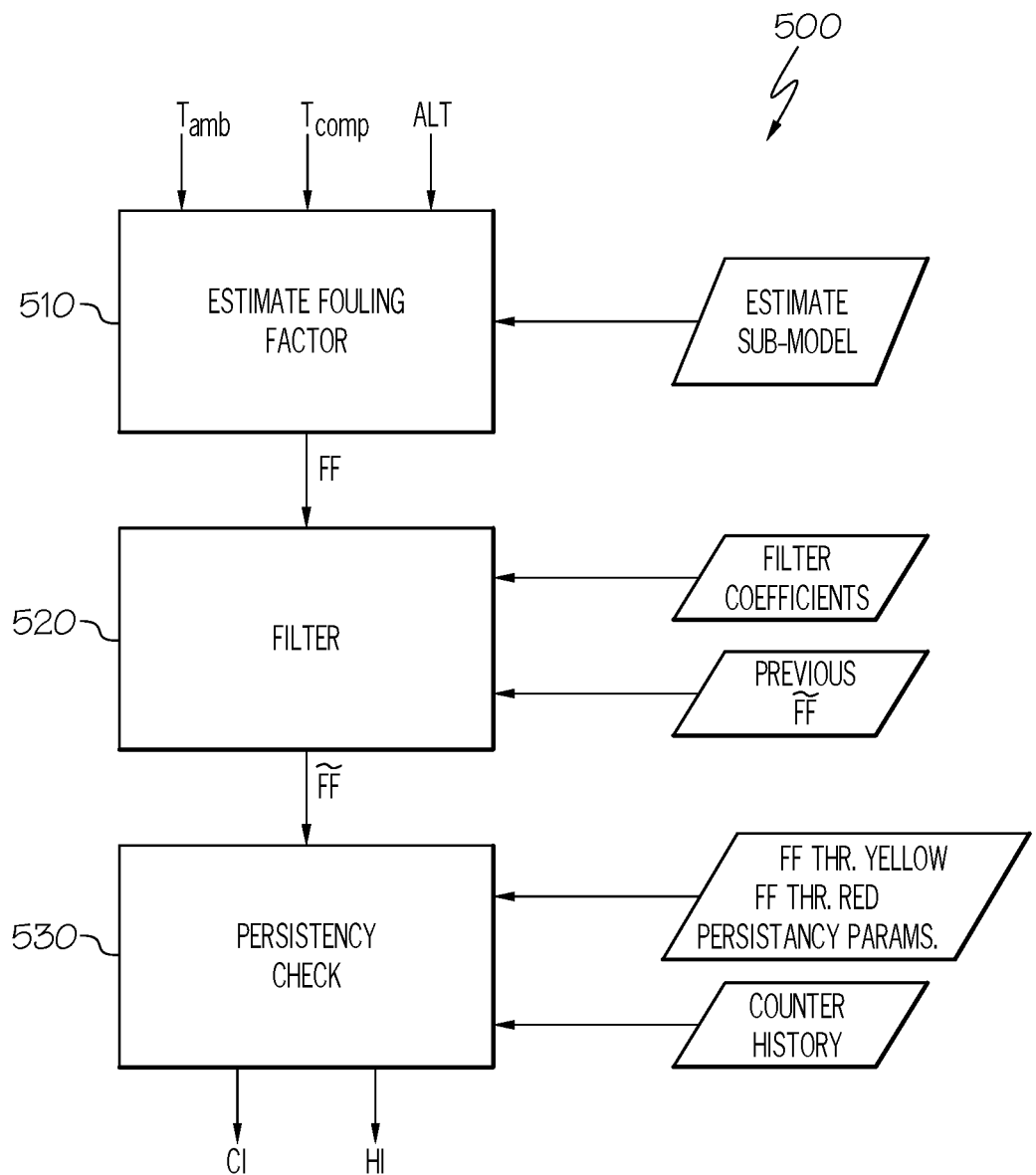
FIG. 5 is a functional block diagram of a fouling module of the maintenance system of FIG. 3 in accordance with another exemplary embodiment.

The fouling module 320 receives the parameters from the data collection module 310. The fouling module 320 includes one or more models 322 formed by algorithms that provide a mathematical framework designed to process the received values to generate data-driven diagnostic and prognostic information associated with one or more of the heat exchangers 210, 212. As such, the model 322 generally represents the correlations or relationships between the noted parameters (e.g., compressor exit temperature ($T_{comp}$), the altitude (Alt), and ambient temperature ($T_{amb}$)) and the present or future condition of the heat exchangers 210, 212, for example, based on empirical data. As shown, the fouling module 320 generates one or more condition indicators and health indicators for one or more of the heat exchangers 210, 212. The model 322 may take various forms. More specific details about the model 322 are provided below with reference to FIGS. 4 and 5, which are presented as processes 400, 500 used to determine the condition indicators and the health indicators. FIGS. 4 and 5 will now be described prior to describing the remaining components of FIG. 3.

As introduced above, FIG. 4 depicts a data flow for process or logic 400 used by the model 322 and/or fouling module 320 in accordance with an exemplary embodiment. The process 400 of FIG. 4 may be considered in the context of logic units or process steps. In a first logic unit 410, baseline compressor exit temperatures ($\hat{T}_{comp}^{0}$) are estimated based on the ambient temperatures ($T_{amb}$) and the altitudes (Alt). The logic unit 410 may utilize a baseline estimate sub-model that associates a respective baseline compressor exit temperature ($\hat{T}_{comp}^{0}$) for a particular set of ambient temperature ($T_{amb}$) and altitude (Alt).

In one exemplary embodiment, the baseline estimate sub-model used by logic unit 410 may incorporate a physics-based first principal model based on previous simulations of compressor exit temperature, ambient temperatures, and altitudes for a "healthy" ECS (fouling factor is zero) at certain operating conditions. In use, upon receipt of data representing ambient temperature and altitude, the compressor exit temperature may be estimated. Such estimations may be performed in a number of different ways, including, multi-dimensional interpolation e.g., two-dimensional look up table for ambient temperature and altitude); polynomial based curve fittings; and/or neural network based function approximations. In further embodiments, the compressor exit temperature may be computed directly from an ECS performance model.

In logic unit 420, the baseline compressor exit temperatures ($\hat{T}_{comp}^{0}$) are compared to the corresponding measured compressor exit temperatures ($T_{comp}$), and the differences between the baseline compressor exit temperatures ($\hat{T}_{comp}^{0}$) and the measured compressor exit temperatures ($T_{comp}$) are generated as compressor temperature residuals ($residual_{T_{comp}}$).

In logic unit 430, the compressor temperature residuals ($residual_{T_{comp}}$) are subject to filtering. The filtering may be based on filter coefficients and previous compressor temperature residuals. Generally, filtering functions to smooth residuals, and filtering coefficients may be applied to the previous historical residuals (e.g., as a form of weighting factors).

In logic unit 440, the filtered compressor temperature residuals ($\tilde{residual}_{T_{comp}}$) are subject to a persistency check. The persistency check may be based on a number of factors, including a counter history, persistency parameters, and residual thresholds for health indicators. Generally, the persistency check may be a kind of latch logic that functions to make the indicators more robust by reducing false alarms. For example, in one embodiment, the persistency check may include determining the number of consecutive cycles that the residuals exceed the threshold value and/or a boundary or persistency check value that trigger the associated condition. In one exemplary embodiment, the logic unit 440 uses these factors to generate one or more alerts, warnings, and/or advisories. For example, if the logic unit 440 determines that the filtered compressor temperature residuals ($\tilde{residual}_{T_{comp}}$) exceed a first threshold, an advisory alert or yellow condition (Fouling_Yellow) may be generated. If the logic unit 440 determines that the filtered compressor temperature residuals ($\tilde{residual}_{T_{comp}}$) exceed a second threshold, a warning alert or red condition (Fouling_Red) may be generated. If the logic unit 440 determines that the filtered compressor temperature residuals ($\tilde{residual}_{T_{comp}}$) does not exceed either threshold, an informational alert or green condition (Fouling_Green) may be generated.

As such, the process 400 may generate a number of values and/or flags as condition and/or health indicators. Typically, a condition indicator corresponds to a derived parameter based on the sensor and other data, and a health indicator is a diagnostic, prognostic, or predictive conclusion based on the condition indicators. As examples, the process 400 may generate the baseline compressor exit temperatures ($\hat{T}_{comp}{}^0$), compressor temperature residuals (residual$_{T_{comp}}$), and filtered compressor temperature residuals (resi$\tilde{d}$ual$_{T_{comp}}$) as condition indicators. The process 400 may generate an advisory alert, warning alert, and/or informational alert as health or condition indicators representing the fouling condition. The condition and/or health indicators may be provided to fusion module 330 and reporting module 340, as described in greater detail below.

As noted above, the advisory alert (or yellow condition) indicates to a crew that the respective heat exchanger is subject to deterioration and that maintenance action should be undertaken within a relatively short amount of time, and the warning alert (or red condition) indicates to a crew that the respective heat exchanger is subject to more serious deterioration and that maintenance action should be undertaken immediately.

FIG. 5 depicts a data flow from a process or logic 500 used by the model 322 and/or fouling module 320 in accordance with another exemplary embodiment. The process 500 of FIG. 5 may be used as an alternative to, or in conjunction with, the process 400 of FIG. 4 discussed above.

Referring to FIG. 5, in a first logic unit 510, an initial or unfiltered fouling factor (FF) is estimated based on the ambient temperatures ($T_{amb}$), the altitudes (Alt), and the measured compressor exit temperatures ($T_{comp}$). In one exemplary embodiment, the fouling factor (FF) is a measure of the degree of fouling of the respective heat exchanger 210, 212. The logic unit 510 may utilize a sub-model that derives or calculates an initial fouling factor (FF) based on a particular set of ambient temperature ($T_{amb}$), altitude (Alt), and compressor temperature ($T_{comp}$). In one embodiment, the first logic unit 510 may have a model or sub-model similar to logic unit 410 discussed above, except that a degree of fouling severity represented by the fouling factor is determined based on ambient temperatures ($T_{amb}$), the altitudes (Alt), and the measured compressor exit temperatures ($T_{comp}$), which may be derived from multi-dimensional interpolation (e.g., the three-dimensions of ambient temperature, altitude, and compressor exit temperature polynomial based curve fittings (e.g., a a polynomial in which fouling factor is a function of compressor exit temperature, altitude, ambient temperature); and/or neural network based function approximations.

In logic unit 520, the fouling factors (FF) are subject to filtering. The filtering may be based on filter coefficients and previous fouling factors (F$\tilde{F}$). In one embodiment, logic unit 520 may be similar to the logic unit 420 discussed above. Upon completion of this step, a filtered fouling factor (F$\tilde{F}$) for a respective heat exchanger is considered the "fouling factor" of the respective heat exchanger.

In logic unit 530, the fouling factors (F$\tilde{F}$) are subject to a persistency check. The persistency check may be based on a number of factors, including a counter history, persistency parameters, and residual thresholds for health indicators. In one embodiment, logic unit 530 may be similar to logic unit 430 discussed above. In one exemplary embodiment, the logic unit 530 uses these factors to generate one or more warnings and/or advisories. For example, if the logic unit 530 determines that the fouling factor (F$\tilde{F}$) exceeds a first threshold, an advisory alert (Fouling_Yellow) may be generated. If the logic unit 530 determines that the fouling factor (F$\tilde{F}$) exceeds a second threshold, a warning alert (Fouling_Red) may be generated. If the logic unit 530 determines that the fouling factor (F$\tilde{F}$) does not exceed either threshold, an informational alert (Fouling_Green) may be generated.

As such, the process 500 may generate a number of values and/or flags as condition and/or health indicators representing the fouling condition. As examples, the process 500 may generate the initial fouling factors (FF) and the fouling factors (F$\tilde{F}$) as condition indicators. The process 400 may generate an advisory alert (or Fouling_Yellow), warning alert (or Fouling_Red), informational alert (or Fouling_Green), and Pack_trip as health indicators. The condition and/or health indicators may be provided to fusion module 330 and reporting module 340, as described in greater detail below.

In each of the processes 400, 500 of FIGS. 4 and 5, the condition and health indicators are generated with compressor exit temperature ($T_{comp}$). This parameter is generally less sensitive to operating conditions, thereby providing a more robust determination of condition and health indicators with fewer false alarms. For example, exemplary embodiments discussed above are less sensitive to operating conditions such as ambient humidity. Additionally, this enables generation of such indicators without additional sensors in the air conditioning packs.

Returning to FIG. 3, the fusion module 330 may receive the condition and health indicators of the fouling module 320. In some embodiments, the fusion module 330 may be omitted and the condition and health indicators may be provided directly to the reporting module 340.

In one exemplary embodiment, the fusion module 330 may fuse the various indicators to confirm, isolate and quantify faults, conditions, and indicators using logical, voting or probabilistic reasoning. For example, in one exemplary embodiment, one or more of the condition and/or health indicators may be generated in a manner other than those described above with reference to FIGS. 4 and 5. Such alternative derivations may be used to increase the confidence in the generated indicators and/or to provide additional indicators.

For example, in one exemplary embodiment, the fouling module 320 and/or other module may derive and/or otherwise calculate a fouling factor, condition indicator, and health indicator associated with the heat exchangers 210, 212 based on one or more pressure sensors. In particular, one or more wireless pressure sensors (e.g., sensors 262 of FIG. 2) may determine the pressure drop of air flow through the heat exchangers 210, 212. A model or table may be used to determine a degree of fouling associated with the measured pressure drop. Other parameters that may be considered are pack bleed temperature and temperature control valve (e.g., valve 236) position. Accordingly, such an alternative derivation may be used by the fusion module 330 to increase the confidence in the generated indicators and/or to provide additional indicators.

In one embodiment, the fusion module 330 functions to fuse evidence from multiple sources (e.g., fouling factor, pressure drop, residuals of compressor exit temperature) for aggregation and generation of an overall indicator (which may be considered a level two condition indicator). For example, if fouling factor and pressure drop are each considered level one condition indicators, various techniques (e.g., fuzzy logic and/or Bayesian reasoning) may be used to fuse these indicators into a further level two indicator. For example, if each level one condition indicator indicates relatively high levels, but not red conditions, the fusion of two level one condition indicators may result in a overall level two condition indicator at the red condition. Similarly, if one level one condition indicator is particularly high and the other is relatively low, the overall level two condition indicator may be a yellow condition.

As such, in one exemplary embodiment, the reporting module 340 receives condition and health indicators from the fouling module 320 and/or the fusion module 330. As noted above, these indicators may include fouling factors and alerts representing the fouling condition of the heat exchangers 210, 212. Generally, the reporting module 340 formats this information for presentation to the user as a user report. One example of such a report that may be presented to the user is provided by the visual display 600 of FIG. 6, which may be rendered on a display device of the user interface 148 of the aircraft 110.

Figure 6:
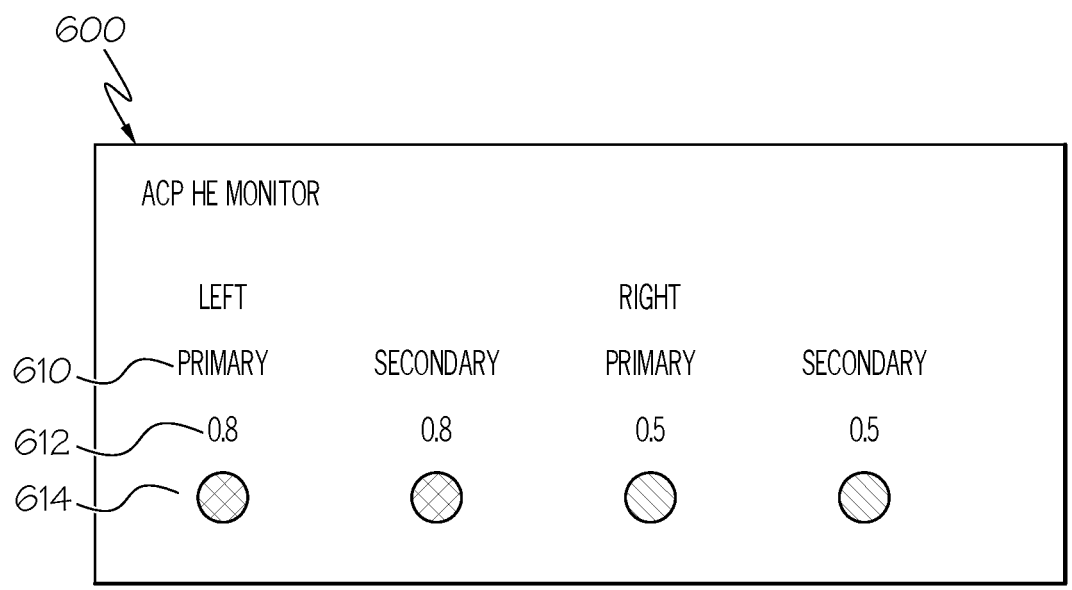
FIG. 6 is an example of a visual display of a report generated by the maintenance system of FIG. 3 in accordance with an exemplary embodiment.

Referring to FIG. 6, the visual display 600 of the user report provides information associated with the condition and health of the heat exchangers 210, 212 of the air conditioning pack (e.g., air conditioning pack 132 of FIG. 1). In this example, the aircraft has two air conditioning packs (e.g., left and right) with primary and secondary heat exchangers for each air conditioning pack, as indicated by label 610. The visual display 600 further provides the fouling factor 612 for each heat exchanger and associated colored symbology 614 representing the alert condition associated with the respective fouling factor 612 (e.g., yellow, red, or green).

As noted above, the communications system 154 of the aircraft 110 may also provide aircraft information to the ground system 160, particularly the ground data server 170. The aircraft information may take various forms. For example, the aircraft information may correspond to the information generated by the maintenance system 140, such as reports that include fouling factors, condition and health indicators, and other aircraft data and operation parameters. In one exemplary embodiment, the ground data server 170 may distribute such reports to the user devices 190, as appropriate. In a further exemplary embodiment, the ground data server 170 may receive aircraft information from a number of aircraft, aggregate and/or summarize the information, and distribute the user reports and/or summaries to the user devices 190, as appropriate.

In a further embodiment, the ground data server 170 may processes the aircraft information to evaluate and/or calculate the condition and health indicators associated with the aircraft 110. In particular, the ground data server 170 may function in lieu of the maintenance system 140 on the aircraft 110 and/or as an alternative the maintenance system 140 on the aircraft 110. In such an embodiment, the ground data server 170 may receive aircraft information from the aircraft 110 (e.g., from the communication unit 154) in the form of a data report, which may include, as examples, exit temperatures from the compressor exit temperature sensors, altitudes, ambient temperatures, pressure drops across the heat exchangers, and any other suitable types of data. In some embodiments, the data report may further one or more of the health and condition indicators discussed above, such as the fouling conditions and/or fouling factors.

Figure 7:
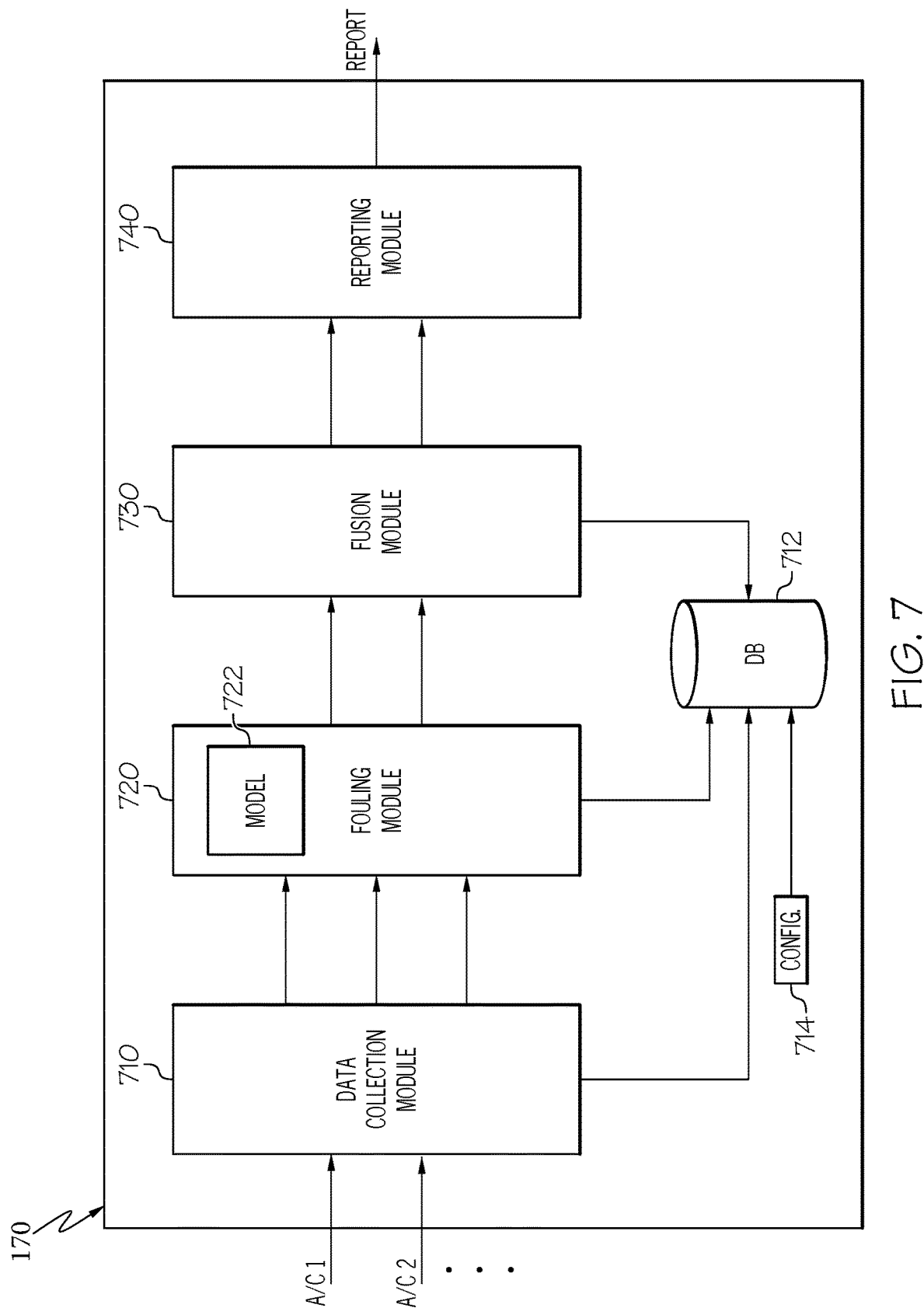
FIG. 7 is a functional block diagram of a ground data server associated with the aircraft management system of FIG. 1 in accordance with an exemplary embodiment.

Additional details about the ground data server 170 are provided with reference to FIG. 7, which is a functional block diagram of the ground data server 170. FIG. 7 depicts the ground data server 170 organized as a number of functional units or modules 710, 720, 730, and 740 (e.g., software, hardware, or combinations thereof). Specifically, each of the modules 710, 720, 730, and 740 may be implemented by the components discussed above in FIG. 1 to carry out specific functions. FIG. 7 depicts one exemplary organization, and other embodiments may perform similar functions with alternative organization or implementation. It should also be noted that, depending on the nature of the aircraft information received and processed by the ground data server 170, one or more of the modules and tasks discussed below may be omitted.

In one exemplary embodiment, the data collection module 710 receives aircraft information associated with one or more aircraft (e.g., aircraft 110). For example, the aircraft information may correspond to information collected by the maintenance system 140, such as a compressor exit temperature ($T_{comp}$), the altitude (Alt), and ambient temperature ($T_{amb}$). Other information may include identification information, pollution characteristics, geographical location, flight path characteristics, engine operating parameters, weather conditions, time dependencies, filter characteristics, historical maintenance data, and other data, as some examples.

In one exemplary embodiment, the data collection module 710 operates in a manner similar to the data collection module 310 of FIG. 3. As appropriate, the data collection module 710 may include any suitable type of conditioning and filtering functionality in order to generate and/or otherwise derive parameters based on the received data. In one embodiment, the data collection module 710 may parse the data, store the data in a database 712, and/or trigger the fouling module 720 that the data is ready for further processing.

The fouling module 720 receives the parameters from the data collection module 710. The fouling module 720 includes one or more models 722 formed by algorithms that provide a mathematical framework designed to process the received values to generate data-driven diagnostic and prognostic information associated with the heat exchangers. As introduced above, the model 722 generally represents the correlations or relationships between the noted parameters (e.g., compressor exit temperature ( ), the altitude (Alt), and ambient temperature ( )) and the condition of the heat exchangers, for example, based on empirical data. The fouling module 720 generates one or more condition indicators and health indicators for the heat exchangers. In one exemplary embodiment, the fouling module 720 operates in a manner similar to the fouling module 320 of FIG. 3 and further depicted in FIGS. 4 and 5.

In some embodiments, the fouling module 720 may access various types of data from the database 712 to generate the condition and health indicators. Such data may include configuration data 714 in the form of identification numbers and/or installation dates of the air conditioning packs and/or heat exchangers. The fouling module 720 may store the condition indicators and health indicators in database 712 and/or provide the condition indicators and health indicators to the fusion module 730.

The fusion module 730 may receive the condition and health indicators of the fouling module 720. In one exemplary embodiment, the fusion module 730 may fuse the various indicators to confirm, isolate and quantify faults, conditions, and indicators using logical, voting or probabilistic reasoning. In one exemplary embodiment, the fusion module 730 operates in a manner similar to the fusion module 330 of FIG. 3. In addition to fusing various indicator associated with a particular aircraft, the fusion module 730 may fuse indicators across a number of aircraft.

In one embodiment, data from multiple aircraft may be used to improve the models and sub-models discussed above. For example, observations of common patterns from trending parameters across a fleet (for example, the parameters are increasing at the same time across whole fleet) may be collected, and this information may be used an additional evidence and for the fusion of condition indicators to adjust the fusion output. Additionally, this enables the prioritization of maintenance actions when there are multiple ECS that need the maintenance simultaneously.

Generally, the reporting module 740 formats this information for presentation to the user as a user report. As noted above, these indicators may include fouling factors, warnings, and/or advisories associated with the heat exchangers. In one exemplary embodiment, the reporting module 740 operates in a manner similar to the reporting module 340 of FIG. 3.

As also introduced above, the reporting module 740 distributes the user reports to the user devices 190. One example of such a report that may be presented to the user is provided by the visual display 800 of FIG. 8, which may be rendered on a display device of the user interface 196 of user device 190.

Figure 8:
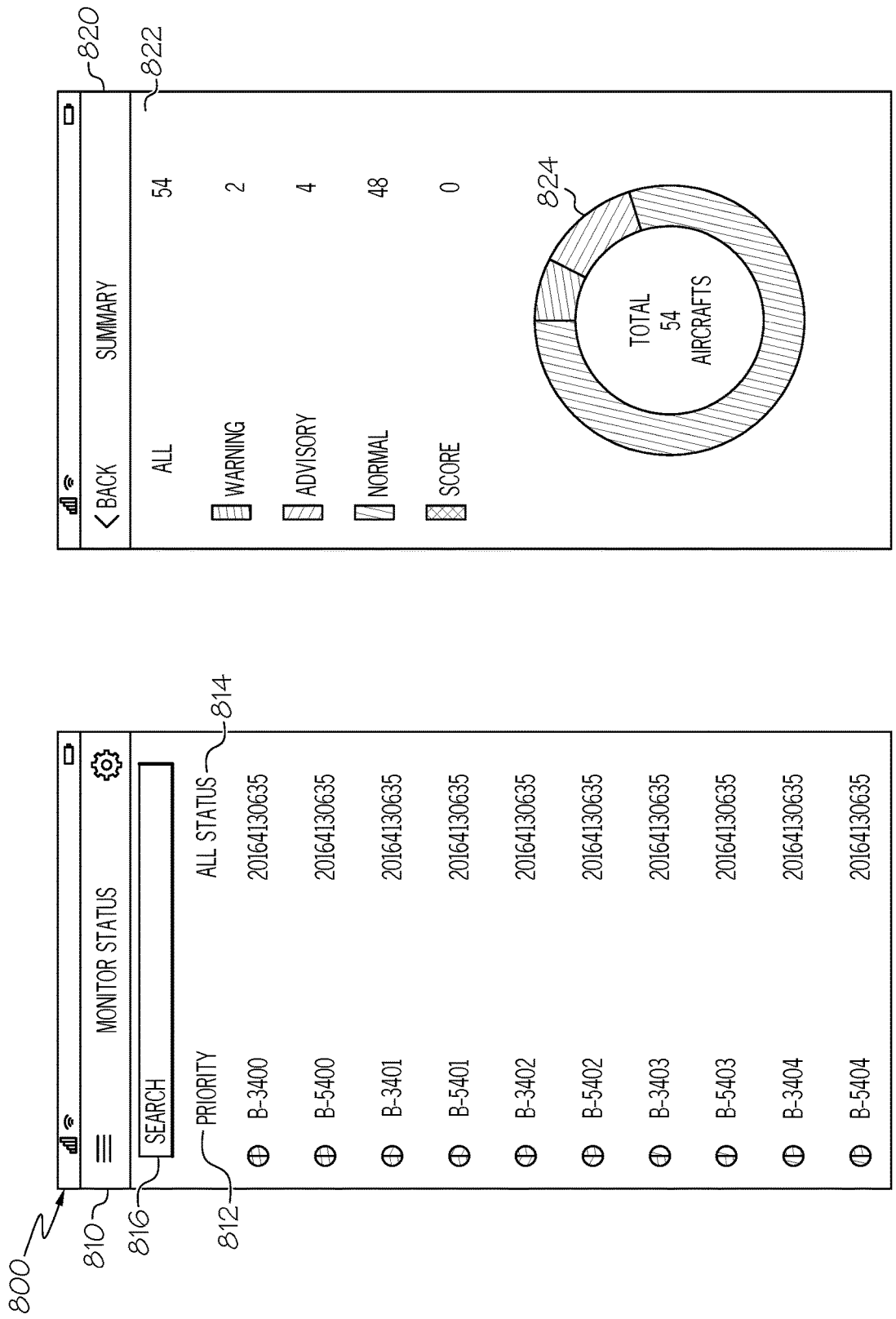
FIG. 8 is an example of a visual display of a report generated by the ground data server of FIG. 7 in accordance with an exemplary embodiment.

The visual display 800 of FIG. 8 may be considered to include first and second portions 810, 820, which may correspond to portions of the same screen or different page views. The first portion 810 presents a group of aircraft listed by identifier, each of which is associated with condition symbology 812. The condition symbology 812 is colored or otherwise rendered to represent the alert or fouling condition of the heat exchangers of the aircraft. As examples, the condition symbology 812 may be colored green for an informational alert (no warning or advisory), yellow for an advisory alert, or red for a warning alert. In the depicted embodiment, the aircraft are listed according to priority, e.g., with the warning conditions at the top, although any manner of listing may be provided.

In one exemplary embodiment, the condition symbology 812 may be segmented to represent the condition of the heat exchangers in more than one air conditioning pack of a particular aircraft. For example, the last aircraft ("B-5404") in the list has symbology 812 in which the left half portion is green and the right half portion is red. This indicates that the heat exchangers in the left air conditioning pack are in an acceptable condition and that the heat exchangers in the right air conditioning pack are in a warning alert. Time stamps 814 are also provided in the list to indicate the timeliness of the condition symbology 812. In particular, the time stamp 814 indicates when the data used to calculate condition and health indicators represented by the condition symbology 812 was generated or downloaded to the ground data server 170 or user device 190. As also depicted in FIG. 8, the first portion 810 may include a search field 816 that enables a user to search and retrieve information associated with a particular aircraft.

The second portion 820 presents summary information regarding the group of aircraft. In particular, the second portion 820 presents the number of aircraft with heat exchangers in each type of condition. Chart 822 presents the summary information in table form. For example, chart 822 indicates the number of aircraft with a warning condition (e.g., 2 aircraft), an advisory condition (e.g., 4 aircraft), and a normal condition (e.g., 48 aircraft). The second portion 820 also presents the summary information in graphical form. In particular, chart 824 provides relative indications of each type of alert condition.

Accordingly, exemplary embodiments enable improved heat exchanger monitoring and maintenance. This provides a maximized life while minimizing unscheduled or unnecessary maintenance and delay costs. Exemplary embodiments estimate conditions such as fouling and maintenance requirements based on correlations between the maintenance and real world usage. Exemplary embodiments provide these advantages without additional sensors or pollution mitigation equipment. Moreover, exemplary embodiments provide these advantages with parameters that are less sensitive to operating conditions. In some embodiments, customers may track fleet status and make recommendations about when to service the heat exchangers on any aircraft.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A vehicle management system, comprising:
an onboard vehicle system arranged onboard a first vehicle, comprising:
  a compressor exit temperature sensor configured to determine a compressor exit temperature at a compressor of an environmental control system (ECS) of the first vehicle;
  a flight data acquisition unit coupled to receive the compressor exit temperature from the compressor exit temperature sensor, an altitude of the first vehicle, and an ambient temperature, and configured to generate a data report containing at least the compressor exit temperature, the altitude, and the ambient temperature; and
  a communications system coupled to receive and transmit the data report from the data acquisition unit; and
a ground system, comprising:
  a ground data server coupled to receive the data report from the communications system, the ground data server configured to determine a fouling condition of an environmental conditioning element of the ECS based on at least the compressor exit temperature, the altitude, and the ambient temperature; and
  a mobile device having a maintenance module running thereon, the maintenance module coupled to receive the fouling condition from the ground data server and configured to provide an interface for displaying the fouling condition to a user on a mobile device,
  wherein the ground data server is configured to estimate a baseline ECS compressor temperature based on the ambient temperature and the altitude and to generate the fouling condition based on residuals of the baseline ECS compressor temperature and the compressor exit temperature from the compressor exit temperature sensor.

2. The vehicle management system of claim 1, wherein the fouling condition represents a degree of fouling severity of the environmental conditioning element.

3. The vehicle management system of claim 2, wherein the environmental conditioning element is a heat exchanger of an air conditioning pack.

4. The vehicle management system of claim 1, wherein the ground data server is configured to filter the residuals with a filter coefficient and to generate the fouling condition further based on the filtered residuals.

5. The vehicle management system of claim 4, wherein the ground data server is configured to perform persistency checks on the filtered residuals and to generate the fouling condition further based on the persistency checks.

6. The vehicle management system of claim 1, wherein the ground data server is configured to generate the fouling condition as an advisory alert when the fouling condition exceeds a first threshold and as a warning alert when the fouling condition exceeds a second threshold.

7. The vehicle management system of claim 1, wherein the ground data server is further configured to generate the fouling condition as a fouling factor represented by a numerical value indicating a severity of fouling, and
wherein the ground data server is configured to estimate a baseline ECS compressor temperature based on the ambient temperature and the altitude, generate residuals of the baseline ECS compressor temperature and the compressor exit temperature from the compressor exit temperature sensor, filter the residuals with a filter coefficient to generate filtered residuals, perform persistency checks on the filtered residuals, and generate the fouling condition further based on the filtered residuals and the persistency checks.

8. The vehicle management system of claim 7, wherein the ground data server is further configured to generate an advisory alert when the fouling factor exceeds a first threshold and a warning alert when the fouling factor exceeds a second threshold.

9. The vehicle management system of claim 8, wherein the maintenance module is configured to generate a user report with the fouling factor.

10. The vehicle management system of claim 1, wherein the ground data server is further configured to receive at least one additional data report from a second vehicle and to generate an additional fouling condition associated with the second vehicle.

11. The vehicle management system of claim 10, wherein the ground data server is further configured to fuse the fouling condition of the first vehicle and the fouling condition of the second vehicle to generate an overall condition indicator.

12. The vehicle management system of claim 11, wherein the maintenance module is configured to generate a user report with the fouling condition of the first vehicle and the fouling condition for the second vehicle.

13. A method, comprising the steps of:
collecting, with an onboard vehicle system for a first vehicle, a compressor exit temperature of a compressor of a heat exchanger of an environmental control system (ECS) of the first vehicle, an altitude of the first vehicle, and an ambient temperature;
generating a data report with the compressor exit temperature, the altitude, and the ambient temperature;
sending the data report with a communications system;
receiving, at a ground data server, the data report from the communications system;
determining a fouling condition of the heat exchanger of the ECS based on at least the compressor exit temperature, the altitude, and the ambient temperature; and
generating a user report on a mobile application interface for displaying the fouling condition to a user on a mobile device,
wherein the determining step includes estimating a baseline ECS compressor temperature based on the ambient temperature and the altitude, and
wherein the generating step includes generating the fouling condition based on residuals of the baseline ECS compressor temperature and the compressor exit temperature from the compressor exit temperature sensor.

14. The method of claim 13,
wherein the receiving step includes receiving, at the ground data server, at least one additional data report from a second vehicle, and
wherein the generating step includes generating an additional fouling condition associated with the second vehicle.

15. The method of claim 13, further comprising fusing the fouling condition of the first vehicle and the fouling condition of the second vehicle to generate an overall condition indicator.

16. The method of claim 15, wherein the generating the user report includes generating the user report with the fouling condition of the first vehicle and the fouling condition for the second vehicle.

17. The method of claim 13, wherein the generating the user report includes generating the fouling condition as an advisory alert when the fouling condition exceeds a first threshold and as a warning alert when the fouling condition exceeds a second threshold.

18. The method of claim 13, wherein the determining step includes determining the fouling condition as a fouling factor represented by a numerical value indicating a severity of fouling.

19. A vehicle management system, comprising:
an onboard vehicle system arranged onboard a first vehicle, comprising:
  a compressor exit temperature sensor configured to determine a compressor exit temperature at a compressor of an environmental control system (ECS) of the first vehicle;
  a flight data acquisition unit coupled to receive the compressor exit temperature from the compressor exit temperature sensor, an altitude of the first vehicle, and an ambient temperature, and configured to generate a data report containing at least the compressor exit temperature, the altitude, and the ambient temperature; and
  a communications system coupled to receive and transmit the data report from the data acquisition unit; and
a ground system, comprising:
  a ground data server coupled to receive the data report from the communications system, the ground data server configured to determine a fouling condition of an environmental conditioning element of the ECS based on at least the compressor exit temperature, the altitude, and the ambient temperature; and
  a mobile device having a maintenance module running thereon, the maintenance module coupled to receive the fouling condition from the ground data server and configured to provide an interface for displaying the fouling condition to a user on a mobile device,
  wherein the ground data server is further configured to:
    receive at least one additional data report from a second vehicle and to generate an additional fouling condition associated with the second vehicle, and
    fuse the fouling condition of the first vehicle and the fouling condition of the second vehicle to generate an overall condition indicator.

20. The system of claim 19, wherein the maintenance module is configured to generate a user report with the fouling condition of the first vehicle and the fouling condition for the second vehicle.

* * * * *